US007008937B2

(12) United States Patent
Bommer (10) Patent No.: US 7,008,937 B2
(45) Date of Patent: Mar. 7, 2006

(54) PORPHYRINS AND METALLOPORPHYRINS FOR INHIBITING HEME IRON UPTAKE

(75) Inventor: Jerry C. Bommer, Franklin, ID (US)

(73) Assignee: Frontier Scientific, Inc., Logan, UT (US)

(*) Notice: Subject to any disclaimer, the term of this patent is extended or adjusted under 35 U.S.C. 154(b) by 0 days.

(21) Appl. No.: 10/859,810

(22) Filed: Jun. 3, 2004

(65) Prior Publication Data
US 2004/0254155 A1  Dec. 16, 2004

Related U.S. Application Data

(60) Provisional application No. 60/477,178, filed on Jun. 10, 2003.

(51) Int. Cl.
*A61K 31/555* (2006.01)
*A61K 31/40* (2006.01)
*A61B 5/055* (2006.01)
*A61B 10/00* (2006.01)

(52) U.S. Cl. .................. 514/185; 514/410; 424/9.362; 424/9.61; 540/145; 534/15

(58) Field of Classification Search ............ 424/9.362, 424/9.61; 540/145; 534/15; 514/185, 410
See application file for complete search history.

(56) References Cited

U.S. PATENT DOCUMENTS 5,223,494 A * 6/1993 Kappas et al. ............... 514/185
6,630,128 B1 * 10/2003 Love et al. ............... 424/9.362

OTHER PUBLICATIONS

Lui, Shu-Qing, Synthesis and Characterization of a Series of Cationic Porphyrins Having Diferent Steric Effects. 2000. Synthetic Communications, 30(11) 2009-2017.*

Gennaro, Alfonso, Remington: The Science and Practice of Pharmacy., 1995, Mack Printing Company. pp. 1447-1462, 1495-1517, 1598-1649.*

Bulcher, J.W., Static Coordination Chemistry and Metalloporphyrins., Elsevier Scientific Publishing Company. 1975. pp. 157-231.*

Guangzhen G. Meng et al., "Porphyrin Chemistry Pertaining to the Design of Anti-Cancer Drugs: Part 2, th Synthesis and in vitro Tests of Water-soluble Porphyrins Containing, in the *meso* Positions, the Functional groups: 4-Mthylpyridinium, or 4-Sulfonatophenyl, in Combination with Phenyl, 4-Pyridyl, 4-Nitrophenyl, or 4-aminophenyl," *Can. J. Chem.*, vol. 72, pp. 2447-2457, 1994.

Yohmei Okuno et al., "An Improved Synthesis of Surfactant Porphyrins," *Georg Thieme Verlag*, pp. 537-539, 1980.

J.W. Buchler, "Static Coordination Chemistry of Metalloporphyrins," *Elsevier Scientific Publishing Company*, pp. 157-231, 1975.

Robert F. Pasternack et al., "On the Aggregation of Meso-Susbituted Water-Soluble Porphryins," *Journal of the American Chemical Society*, pp. 4511-4517, Jun. 28, 1972.

* cited by examiner

*Primary Examiner*—James O. Wilson
*Assistant Examiner*—Matthew L. Fedowitz
(74) *Attorney, Agent, or Firm*—Madson & Metcalf (57) ABSTRACT

The present invention provides a class of porphyrins and metal chelated porphyrins for use as inhibitors of heme iron uptake. The porphyrin/metal chelated porphyrin molecules of the invention are tetra-positively charged porphyrins based on meso-tetra(4-pyridyl)porphines. Several such agents are shown herein to cause inhibition of iron uptake in vivo and in vitro. The invention further provides therapeutic compositions including the porphyrins and/or metalloporphyrins of the invention. In addition, methods of inhibition of heme iron uptake in vivo are taught, as well as methods of treatment of diseases characterized by iron-overload. These methods include the administration of a porphyrin or metalloporphyrin in a therapeutic composition of the invention to prevent uptake of heme iron, thus preventing replenishment of a patient's iron stores.

18 Claims, 7 Drawing Sheets

| Table 1: Assay of Compounds | | | |
|---|---|---|---|
| | Compound | % Inhibition at 800 micromolar | Conc. (micromolar) resulting in 50% inhibition |
| 1 | meso-tetra(N-methyl-4-pyridyl) porphine abbreviated TMP | >50% | 100 |
| 2 | meso-tetra(N-butyl-4-pyridyl) porphine | >50% | 100 |
| 3 | meso-tetra(N-hexyl-4-pyridyl) porphine | Toxic | |
| 4 | meso-tetra(N-methyl-3-pyridyl) porphine | 18% | |
| 5 | meso-tetra(N-methyl-2-pyridyl) porphine | 15% | |
| 6 | meso-tetra(N-ethanol-4-pyridyl) porphine | 20% | |
| 7 | meso-tetra(N-2,3-propanediol-4-pyridyl) porphine | None | |
| 8 | meso-tetra(4-N,N,N-trimethyl anilinium)-porphine | 26% | |
| 9 | Cu(II) meso-tetra(N-methyl-4-pyridyl)porphine | >50% | 100 |
| 10 | Zn(II) meso-tetra(N-methyl-4-pyridyl)porphine | >50% | 120 |
| 11 | Ni(II) meso-tetra(N-methyl-4-pyridyl)porphine | >50% | 160 |
| 12 | Cr(III) meso-tetra(N-methyl-4-pyridyl)porphine | >50% | 4 |
| 13 | Fe(III) meso-tetra(N-methyl-4-pyridyl)porphine | >50% | 40 |
| 14 | Co(III) meso-tetra(N-methyl-4-pyridyl)porphine | >50% | 50 |
| 15 | Ga(III) meso-tetra(N-methyl-4-pyridyl)porphine | >50% | 200-400 |
| 16 | Eu(III) meso-tetra(N-methyl-4-pyridyl)porphine | 45% | |
| 17 | Mn(III) meso-tetra(N-methyl-4-pyridyl)porphine | 37% | |
| 18 | Sn(IV) meso-tetra(N-methyl-4-pyridyl)porphine | None | |

| Table 2: Inhibitory Concentration of TMP Derivatives ||
|---|---|
| Compound | 50% Inhibitory Concentration µM |
| Cr - TMP (#24) | 4 |
| Fe(III)-TMP (#18) | 40 |
| Co-TMP (#25) | 50 |
| TMP (#0) | 100 |
| Ni-TMP (#26) | 160 |
| Cu-TMP (#13) | 100 |
| Zn-TMP (#22) | 120 |
| Ga-TMP (#30) | 200-400 |
| Eu-TMP (#31) | 800 |
| Sn(IV)-TMP (#14) | >800 |
| Mn-TMP (#26) | >800 |

PORPHYRINS AND METALLOPORPHYRINS FOR INHIBITING HEME IRON UPTAKE

CROSS-REFERENCED RELATED APPLICATIONS

This application claims the benefit of U.S. Provisional Application No. 60/477,178, filed Jun. 10, 2003.

STATEMENT REGARDING FEDERALLY SPONSORED RESEARCH

This invention was made with government support under Grant Number 1R43HL65007-01 awarded by the National Heart, Lung, and Blood Institute of the National Institutes of Health of the U.S. Department of Health and Human Services. The Government has certain fights to this invention.

BACKGROUND OF THE INVENTION

The present invention relates to agents for use in the prevention and treatment of iron overload disease states. More specifically, the present invention relates to a class of porphyrins and metalloporphyrins that inhibit heme iron uptake.

Iron overload syndromes are a significant cause of morbidity and mortality throughout the world. In the United States alone, about one in every 250 suffers from one such disease, hemochromatosis, which is a hereditary disease characterized by overabsorption of iron by the intestine. Iron overload is also associated with other diseases including, but not limited to, thalassemia and sickle cell anemia. In part, the iron overload often associated with sickle cell anemia and thalassemia may be attributed to iron acquired from frequent blood transfusions. Patients found to be afflicted with such disorders are often faced with a daunting prescription of treatments with unpleasant side effects and a food supply widely fortified with iron which may serve to counter the good done by any remedy used. In the developed world, two thirds of the iron that is absorbed by a patient is generally derived from heme (or "organic iron"), often present in foods such as red meats, rather than from inorganic iron. In some individual cases of iron overload disease, the disease may also in part be attributed to a high dietary intake of iron.

Iron overload disorders are often difficult to diagnose. This difficulty often arises from the fact that the symptoms presented by many such disorders are often vague and shared with a host of other common diseases. Some of these symptoms include joint pain, fatigue, and abdominal pain. In addition, since it was long believed that iron overload disorders were rare, alternative diagnoses were often favored by physicians. When such a disorder is suspected, however, relatively simple blood tests such as a transferrin saturation test may be performed to measure levels of blood iron and ferritin (a protein indicative of levels of iron stores in the body), and thus confirm or reject the diagnosis. In some cases, patients may be counseled to undergo further testing, possibly including a liver biopsy and/or genetic testing to assure the diagnosis.

Overload of iron in the body leads to deposition of iron in tissues, eventually damaging them if allowed to progress. Joints may be subject to damage, as well as organs such as the pancreas, liver, and heart. When diseases characterized by iron overload go undiagnosed, medical problems including heart disease, arthritis, diabetes, and liver cancer may result.

Once diagnosed, traditional methods of treatment of many iron overload disorders call for the creation and maintenance of a mild anemia in a patient to draw stored iron out of body tissues by incorporating it into new red blood cells. Iron is normally eliminated from the body in minute amounts by the shedding of skin, and by loss of blood. Thus, many traditional methods of treating iron overload syndromes call for the physical removal of iron from the system of a patient using systematically-repeated phlebotomy. Following phlebotomy, stored iron is mobilized for incorporation into new hemoglobin produced in new red blood cells formed to replace those removed with the patient's blood. The patient's blood is monitored throughout the course of treatment to evaluate the levels of iron present in the patient's body and the level of anemia induced by the treatment. Repeated withdrawal of blood eventually depletes the patient's excess stores of iron. Once this has been accomplished, the frequency of phlebotomy may be greatly reduced, with many patients requiring only 2–6 phlebotomies per year following the initial de-ironing process. The initial de-ironing stage may last from less than six months to several years, however.

Such regimens of phlebotomy are generally not an option in patients already exhibiting anemia, however. Similarly, in some patients having iron overload-induced cardiac failure, blood loss such as that caused by phlebotomy can present a significant problem. Further, in individuals with iron-overload due to ineffective erythropoesis or transfusion dependence, removal of iron by phlebotomy may often prove problematic since the individuals are already critically anemic. As a result, therapies involving phlebotomy are not suitable for use with all patients.

An alternative therapy for reducing organic iron stores has become available for use with some such patients for whom phlebotomy would be unsuitable. In this alternative therapy, a patient is administered a chemical chelating agent known as deferoxamine. Deferoxamine binds with iron in the bloodstream, producing a complex that is then removed from the bloodstream by the kidneys and excreted from the patient's body with urine. In some instances, deferoxamine is administered to a patient as a subcutaneous injection, in others, as a continuous infusion delivered by an infusion pump. Deferoxamine has known side effects, however, and may be damaging to individuals with kidney disease. In addition, for some individuals, the anemia induced by deferoxamine treatments may be severe enough to prevent further phlebotomy, while still failing to effectively remove the excess iron from the patient's body.

Deferoxamine is currently the only available drug treatment for iron-overload syndromes. Deferoxamine is limited in its efficacy by its poor oral absorption. It is also rapidly metabolized in the plasma. As a result of this, deferoxamine is generally administered to a patient by continuous subcutaneous infusion. Adverse effects of deferoxamine treatment may include skin discoloration, ocular and auditory abnormalities, sensor motor neurotoxicity, altered renal function, difficulty breathing, muscle cramping, and pulmonary toxicity. In addition, growth retardation has been observed in some children on long-term deferoxamine treatment. These side effects may be ameliorated by the use of slow continuous infusion administration methods. Unfortunately, however, patient compliance with slow continuous infusion regimes is often a problem.

In addition to the inconvenience and side effects, deferoxamine treatment is only partially effective in treating iron overload syndromes. More specifically, while deferoxamine appears able to slowly decrease iron stores in iron-overloaded individuals, it does not act to prevent continued intake of iron from the intestine. This may allow continual replenishment of the iron stores, countering the benefits of the treatments, and thus increasing their length.

It is thus observed that there is a clear need in medicine for more effective therapies and therapeutic agents for use in treating medical conditions associated with iron overload. Since in most cases the iron ingested is present in a patient's body in an accessible form as heme-iron, an inorganic iron-chelating agent is useful to actively reduce iron stores in a patient's body. The utility of such compounds is lessened, however, by the inability to prevent replenishment of bodily stores of iron. Indeed, there are to date no means available for decreasing the absorption of heme by a patient except for strict dietary restrictions, including absolute avoidance of all meat and of plant products containing heme. Such restrictions are often difficult for patients to implement and adhere to since even plant-based foodstuffs often contain cytochromes—proteins often containing heme. It would thus be beneficial to provide a composition for inhibiting heme iron absorption by a patient. Such compositions could render phlebotomy or chelating therapies more effective. In addition, such compositions could potentially serve to help patients afflicted with iron overload maintain healthy levels of iron after initial de-ironing is completed using more traditional therapies.

In some circumstances, a heme iron uptake inhibitor could be used to increase the effectiveness of known or currently unknown chelation therapies by reducing the input of new iron into the system of a patient. This could be implemented while currently known therapies such as monitored phlebotomy or the administration of deferoxamine or other chelating agents are used to remove the currently existing iron stores. Further, a heme-iron uptake inhibitor could potentially be used concurrently with or at the initiation of a transfusion program for sickle cell anemia, thalassemia, or another disorder requiring frequent transfusions of blood in order to limit the patient's iron acquisition to that of the transfusion. Such an inhibitor may also be useful as a preventative agent to reduce the intake of iron and reduce the iron burden in the diseases outlined above. Such agents would thus be beneficial for the use of a previously-de-ironed patient seeking to avoid subsequent re-accumulation of iron. Finally, such an inhibitor may be useful in the treatment of other conditions in which high levels of iron may be harmful, including severe cardiac disease or hemochromatosis heterozygotes in which mild iron excess has been demonstrated to lead to coronary artery disease.

BRIEF SUMMARY OF THE INVENTION

The present invention has been developed in response to the present state of the art, and in particular, in response to the problems and needs in the art that have not yet been fully solved by currently available treatments for iron overload disorders such as, but not limited to, hemochromatosis. Thus, the present invention provides a family of novel agents for inhibiting heme iron uptake, and thus, for preventing or treating iron overload diseases and for maintaining iron levels in patients previously treated for such disorders. The present invention further provides therapeutic compositions including the novel uptake-inhibiting porphyrin and metalloporphyrin agents of the invention. The invention also provides methods of inhibiting heme iron uptake in a human or non-human mammal. Further, the invention provides methods of treating diseases characterized by iron overload using uptake-inhibitory agents of the invention or therapeutics according to the invention containing such inhibitory agents.

Figure 1A:
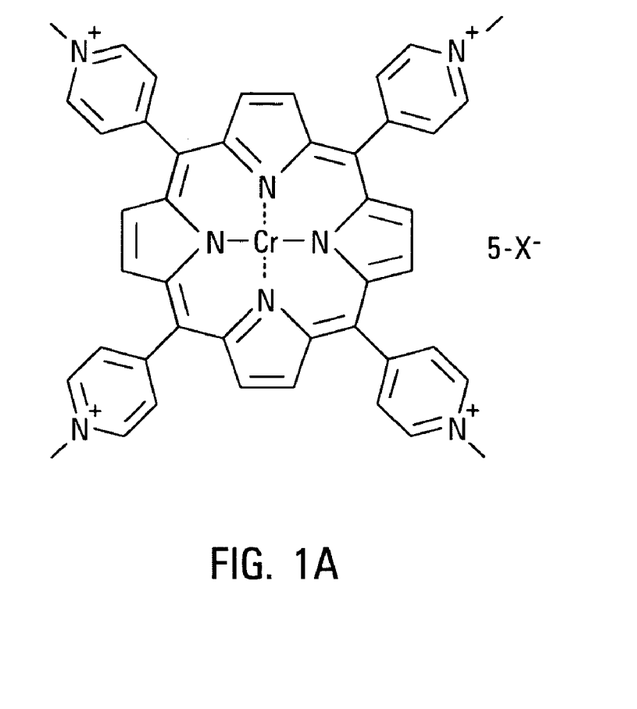
FIG. 1A provides a structural representation of Cr (III) meso-tetra(N-methyl-4-pyridyl) porphine, or "Cr-TMP," a metalloporphyrin of the invention.
Figure 1B:
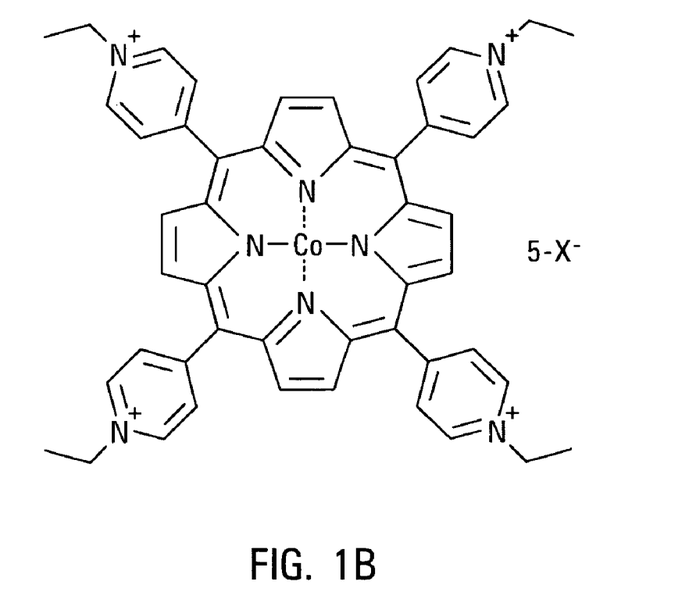
FIG. 1B provides a structural representation of Co (III) meso-tetra(N-ethyl-4-pyridyl) porphine, a metalloporphyrin of the invention.

The invention provides a family of positively-charged porphyrins having the general formula: 5,10,15,20-tetrakis (1-alkyl-4-pyridyl)-21H,23H-porphine. These agents are alternatively referred to meso-tetra(N-alkyl-4-pyridyl) porphines. Several exemplary members of this family are illustrated in FIGS. 1A and 1B. Porphyrins are macrocyclic molecular compounds with a ring-shaped tetrapyrrolic core. As such, porphyrins are commonly found in their dianionic form coordinated to a metal ion. The unique properties of the tetrapyrrolic core have made porphyrins central in many biological systems that play a vital role in many life processes. Several compounds that are critically important for essential biological processes, such as chlorophyll and heme, are derived from the coordination of a metal ion with a porphyrin nucleus. H. R. Mahler and E. H. Cordes, *Biological Chemistry*, 2d ed. 418, 1966.

Porphyrins are generally derived from the parent tetrapyrrole porphin by replacing hydrogens at one or more of the positions 1 and 8 as well as at one or more of the meso- (pyrrole bridging) carbon atoms with side chains such as, for example, methyls, ethyls, vinyls, propionic acids, or aromatic groups. Id. Porphyrins are often classified based on the side chains they contain. Hydrogenation of one or two pyrrole moieties generates the corresponding chlorin, and, respectively, bacteriochlorin derivatives.

As briefly noted above, porphyrins are able to form metal chelates with a large variety of metal ions, including chromium (see FIG. 1A), cobalt (see FIG. 1B), copper, iron, magnesium, nickel, silver, and zinc. Id. at 419. As discussed further below, porphyrins may also chelate with gallium, europium, manganese, and tin. Heme is an iron chelate of a porphyrin, while chlorophyll and bacteriochlorophyll are magnesium chelates. Porphyrins such as these are generally synthesized from the precursors glycine and succinyl CoA. See L. Stryer, *Biochemistry*, 2d ed., 504–507 (1981).

Within the scope of the invention, the alkyl group referred to in the general equations may be methyl through butyl. Variations are illustrated in FIGS. 1A and 1B. In addition to the above agents, certain of the metal chelates of the above porphyrins may be useful, including, but not limited to, nickel, copper, zinc, iron, cobalt, chromium, magnesium, silver, gallium, europium, manganese, and tin chelates. The porphyrin agents of the invention are generally water soluble. As a result, they may be delivered by a variety of pathways, including conventional pharmaceutical forms such as solid oral dosage forms such as tablets, and liquid forms such as suspensions, solutions, beverages, etc. In addition, they may be provided in a variety of forms to simplify their long-term regular use such as in drinks, foods, sauces, condiments, or seasonings to accompany meals, especially those featuring iron-rich foods such as meat dishes. The porphyrins of the invention are generally poorly absorbed by the body of a patient. In many cases, however, the porphyrins and metalloporphyrins of the invention inhibit the uptake of heme-iron in vivo in the rat intestinal model, and inhibit the uptake of heme-iron by small intestinal derived cells in in vitro experiments at exceedingly low concentrations. One active compound tested, CrTMP, showed no toxicity in two cell lines when tested at a high concentration relative to its contemplated therapeutic dosage. Herein, the abbreviation "TMP" is used to describe meso-tetra(N-methyl-4-pyridyl) porphine.

The porphyrins of the invention may be coupled with various pharmaceutically acceptable anions for use in therapeutic compositions. Such therapeutic compositions are useful in methods of inhibiting iron uptake. Such methods may be practiced to prevent accumulation of the iron burden that otherwise develops in a patient having a disease state characterized by iron overload. This may be useful in a patient that has previously undergone de-ironing. Further, such therapeutic compositions may be useful in methods of treating iron overload diseases by being used concurrently with a primary iron removal therapy such as phlebotomy or chelation therapy to prevent replenishment of a patient's iron stores during therapy by heme uptake.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the instant invention may be best understood by reference to the detailed description which follows, the appended claims, and the included Figures. The following more detailed description of the embodiments of the method of the present invention, as represented in FIGS. 1 through 12, is not intended to limit the scope of the invention, as claimed, but is merely representative of presently preferred embodiments of the invention.

The invention thus provides a class of tetra-positively-charged porphyrins and metalloporphyrins based upon meso-tetra(4-pyridyl) porphines, therapeutic compositions containing these molecules, and methods of their administration to a human or non-human animal to inhibit heme iron uptake in in vivo, as well as in vitro, iron uptake inhibition methods. More specifically, the invention first provides a family of meso-tetra(N-alkyl-4-pyridyl) porphines and their metal chelates such as those illustrated in FIGS. 1A and 1B for use in the prevention and/or treatment of iron overload disorders such as hemochromatosis. Suitable chelates include porphyrins of the invention chelated with nickel, copper, zinc, iron, cobalt, chromium, magnesium, silver, gallium, europium, manganese, and tin. Other suitable porphyrin chelates will be known to one of skill in the art.

In some embodiments of the invention, the alkyl group of the meso-tetra(N-alkyl-4-pyridyl) porphines may be a methyl, ethyl, propyl, or butyl group. In some specific molecules within the scope of the invention, the propyl is n-propyl or isopropyl. In other specific molecules within the scope of the invention, butyl is n-butyl, isobutyl, or t-butyl.

The meso-tetra(N-alkyl-4-pyridyl) porphine agents of the present invention may be synthesized as pharmaceutically acceptable salts for incorporation into therapeutic compositions. Without being limited to any one theory, it is expected that for a therapeutic composition comprising a form of a porphyrin of the invention such as a pharmaceutically acceptable salt, the counter-ions used will generally not be critical to the activity of the porphyrin, and thus may be selected from a broad range of pharmaceutically-acceptable counterions, including, for example, chloride, bromide, etc.

The term "pharmaceutically acceptable salts," as used herein, refers to salts of the agents of the invention that are substantially non-toxic to living organisms. Typical pharmaceutically acceptable salts include those salts prepared by reaction of the agents of the invention with a pharmaceutically acceptable mineral or organic acid, or a pharmaceutically acceptable alkali metal or organic base, depending on the substituents present on the agents of the invention.

Examples of pharmaceutically acceptable mineral acids which may be used to provide the needed counterions and thus to prepare pharmaceutically acceptable salts include: hydrochloric acid, phosphoric acid, sulfuric acid, hydrobromic acid, hydroiodic acid, phosphorous acid and the like. Examples of pharmaceutically acceptable organic acids which may be used to prepare pharmaceutically acceptable salts include aliphatic mono and dicarboxylic acids, such as oxalic acid, carbonic acid, citric acid, succinic acid, phenyl-substituted alkanoic acids, aliphatic and aromatic sulfuric acids and the like. Pharmaceutically acceptable salts prepared from mineral or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts will be known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts will be known to one of ordinary skill in the art.

It should be recognized that the particular anion or cation forming a part of any salt of this invention is not critical, so long as the salt, as a whole, is pharmacologically acceptable and as long as the anion or cationic moiety does not contribute undesired qualities or effects. Further, additional pharmaceutically acceptable salts are known to those skilled in the art, and may be used within the scope of the invention. Pharmaceutically acceptable salts are discussed in detail in *Pharmaceutical Salts: Properties, Selection and Use—A Handbook*, by C. G. Wermuth and P. H. Stahl, Verlag Helvetica Chimica Acta, 2002, which is incorporated herein by reference.

It should be additionally noted that the agents of the invention may be combined with a pharmaceutically acceptable carrier to provide therapeutic compositions for treating biological conditions or disorders such as those briefly noted herein. Such compositions may be used in humans, as well as in non-human mammalian patients.

The particular carrier employed in these therapeutic compositions may take a wide variety of forms selected based upon the type of administration method desired for the composition. Some common routes of administration include, but are not limited to, subcutaneous, intramuscular, intravenous, oral, topical, suppository and parenteral. The compositions of the invention are generally administrated orally. Therapeutic compositions typically contain from about 0.1 to about 90% by weight (such as 1 to 20% or 1 to 10%) of a therapeutic agent such as the porphyrins and metalloporphyrins of the invention in a pharmaceutically acceptable carrier.

In one example, a therapeutic composition may take the form of a solid oral dosage form such as a tablet, capsule, powder, etc., including the porphyrins and/or metalloporphyrins of the invention. Solid formulations of the compositions for oral administration may contain suitable carriers or excipients, such as corn starch or other starches, gelatin, lactose or other sugars, acacia, sucrose, microcrystalline cellulose, kaolin, sodium chloride, alginic acid, and any of a well-known family of diluents, granulating agents, lubricants, binders, disintegrating agents, and the like. Disintegrators that can be used include, without limitation, microcrystalline cellulose, corn starch, sodium starch glycolate, and alginic acid. Tablet binders that may be used include acacia, methylcellulose, sodium carboxymethylcellulose, polyvinylpyrrolidone (Povidone™), hydroxypropyl methylcellulose, sucrose, starch, and ethylcellulose. Lubricants that may be used include magnesium stearates, stearic acid, silicone fluid, talc, waxes, oils, and colloidal silica. Due to their ease of administration, tablets and capsules may represent an advantageous oral dosage form for the therapeutic compositions of the present invention.

Liquid formulations of the compositions for oral administration may take the form of suspensions, elixirs, solutions, or the like. In these, typical pharmaceutical media such as water or other aqueous vehicles, glycols, oils, alcohols, wetting agents, flavoring agents, preservatives, coloring agents, and similar such ingredients may be utilized in combination with the active compound or compounds. In addition, such liquid formulations may contain various suspending agents such as methylcellulose, alginates, tragacanth, pectin, kelgin, carrageenan, acacia, polyvinylpyrrolidone, and polyvinylalcohol.

In addition, the porphyrin and metalloporphyrin components of the invention may be administered in conveniently-consumed forms such as a granular formulation applied to food like a seasoning. Indeed, such compounds could be combined with traditional salts, spices, and other seasonings for administration. Similarly, the porphyrin and metalloporphyrin compounds may be incorporated into sauces and dressings for administration. The high water solubility of many of the compounds of the invention may be administered in a drinkable form such as a beverage, either provided in a pre-prepared form or as a powdered drink mix prepared for consumption by an end user. As above, such a beverage may include any of a variety of additional components to provide a desired taste, color, or even thickness for the beverage.

Other conventional methods, known to those of ordinary skill in the art of medicine, may also be used to administer the therapeutic compositions to the patient. Regardless of the route of administration, the therapeutic agent typically may be administered at a daily dosage of 0.01 mg to 30 mg/kg of body weight of the patient (such as, for example, 1 mg/kg to 5 mg/kg). The therapeutic compositions can be administered in a single dose, or in multiple doses per day if desired to achieve the total desired daily dose. The porphyrins and metalloporphyrins of the invention generally exhibit a low uptake, and thus have a relatively short half-life in the intestinal lumen. Thus, according to some methods of the invention it may be advantageous to administer the compounds of the invention with meals. As such, the dosage amount may instead be keyed to the size of the meal consumed and/or the iron content of the meal. As recognized by those skilled in the art, the particular quantity of therapeutic composition according to the present invention administered to a patient will depend upon a number of factors, including, without limitation, the condition of the patient, and tolerance for the drug.

As briefly described above, the invention further provides methods of inhibiting the absorption of iron in a human or a non-human mammal. Such methods are useful to prevent accumulation of iron in the human or non-human mammal. As such, they may be especially appropriate in a human or non-human mammalian patient following primary de-ironing treatment to prevent re-accumulation of iron in the patient's body by preventing the absorption of heme. In these methods, a tetra-positively charged porphyrin according to the invention, having the formula 5,10,15,20-tetrakis (1-alkyl-4-pyridyl)-21H,23H-porphine, wherein the alkyl is selected from the group consisting of methyl, ethyl, propyl, and butyl, is administered to the human or non-human mammal in need of such treatment. As noted above, the porphyrin or metalloporphyrin may be administered as part of a therapeutic composition, and thus may contain other compounds to aid in administration such as diluents, etc.

As discussed above, in the porphyrins administered in these methods, propyl may be n-propyl or isopropyl; and butyl may be n-butyl, isobutyl, or t-butyl. Further, the porphyrin administered may be either base porphyrin TMP disclosed herein or a metal chelated porphyrin, or a mixture of base porphyrin and at least one (and potentially multiple) metalloporphyrins. Some metalloporphyrins of the invention include Cu(II), Zn(II), Ni(II), Cr(III), Fe(III), Co(III), Ga(III), Eu(III), Mn(III), and Sn(IV) chelates. In such metalloporphyrins, as in the base porphyrins discussed above, propyl may be n-propyl or isopropyl; and butyl may be n-butyl, isobutyl, or t-butyl.

In addition to the methods of preventing heme iron uptake discussed above, the invention further provides methods of treating an iron-overload disease in a human or a non-human mammal. In these methods, a primary de-ironing treatment is pursued in coordination with the administration of a tetra-positively charged porphyrin having the formula 5,10, 15,20-tetrakis(1-alkyl-4-pyridyl)-21H,23H-porphine, wherein the alkyl is selected from the group consisting of methyl, ethyl, propyl, and butyl; to the human or non-human mammal in need of such treatment. In these methods, the primary de-ironing treatment operates to actively deplete the body's iron stores, while administration of the porphyrins and/or metalloporphyrins of the invention operates to prevent replenishment of the patient's iron stores. As such, the administration of the porphyrins and/or metalloporphyrins of the invention may be timed to precede the de-ironing regimen, run concurrent with the regimen, and/or occur or continue past the completion of the primary de-ironing treatment.

Administration of the porphyrins and/or metalloporphyrins of the invention (potentially via a therapeutic composition such as those discussed above) preceding a primary de-ironing treatment such as phlebotomy or chelation therapy may serve to cease or reduce heme uptake, thus ending additional iron accumulation prior to a first phlebotomy visit or chelation treatment initiation. Administration during the course of active de-ironing therapy such as during a regimen of scheduled phlebotomies or chelation therapies may speed the removal of iron by preventing incremental replenishment of iron stores by the uptake of heme from food ingested by the patient. Administration of a porphyrin or metalloporphyrin of the invention following primary de-ironing may serve as a maintenance therapy to control and/or stabilize the heme levels in a patient following successful de-ironing.

As discussed, in such methods, the primary de-ironing treatment used may be serial phlebotomy, chelation therapy conducted using a chelating agent, or another such similar method known to one of ordinary skill in the art. One common chelating agent used in such treatments is deferoxamine. Similar to those treatments discussed above, in the porphyrins and/or metalloporphyrins of the invention, the propyl may be n-propyl or isopropyl; and butyl may be n-butyl, isobutyl, or t-butyl. Further, when the porphyrin is a metal chelated porphyrin, it may be a metal chelate of a metal selected from the group consisting of Cu(II), Zn(II), Ni(II), Cr(III), Fe(III), Co(III), Ga(III), Eu(III), Mn(III), and Sn(IV). In these metalloporphyrins, as in the porphyrins above, propyl may be n-propyl or isopropyl; and butyl may be n-butyl, isobutyl, or t-butyl.

The effectiveness of the method of treatment may be assessed by monitoring the patient for known signs or symptoms of iron overload. As briefly discussed above with regard to diagnosis of disorders characterized by iron overload, a patient may be assessed for iron overload using relatively simple blood tests. One suitable test is a transferrin saturation test. This test may be performed to measure levels of blood iron and ferritin (a protein indicative of levels of iron stores in the body). Thus, either during active de-ironing or during maintenance of previously-attained de-ironing, a patient may be tested to assess the change in blood iron and ferritin. Such measurements may indicate the success of a de-ironing treatment. Further, such tests may be used to monitor the stored iron in a patient following active de-ironing during a maintenance regimen.

The porphyrins of the invention generally include 5,10, 15,20-tetrakis(1-alkyl-4-pyridyl)-21H, 23H-porphines (also referred to as meso-tetra(N-alkyl-4-pyridyl) porphines. These tetra-positively-charged porphines of the invention are generally water soluble, but may be poorly absorbed. The porphyrins of the invention have been shown to inhibit the uptake of heme-derived iron in vivo in a rat intestinal model. The porphyrins of the invention have further been shown to inhibit heme iron uptake in in vitro experiments utilizing cells derived from small intestine.

Various embodiments of the porphyrins of the invention will be discussed in detail in the Examples section which follows. These examples depict only typical embodiments of the invention, and are not to be considered to be limiting of its scope.

EXAMPLES

Example 1

Inhibition of in Vitro Uptake of Radiolabeled Iron from Heme

In a first assay, confluent monolayers of IEC-6 cells were incubated with radioactive iron-labeled heme. IEC-6 cells are transparent epitheloid cells which commonly grow as monolayers that are derived from normal rat small intestine. In this assay, the heme had been previously solubilized in taurodeoxycholate micelles. Twelve-well tissue culture plates were used with 1 ml of phosphate-buffered saline (or "PBS") containing Ca, Mg and glucose. Cells were incubated with the heme solution and a designated inhibitor for times indicated at a temperature of 37° C.

After incubation, the cells were washed with 1 ml of the same buffer at 4° C. three times. The cells were then solubilized by the addition of 1 ml of water and sonicated for 10 minutes in a Branson sonicator. The cells were removed by titration and transferred to 75 ml tubes. Subsequently, the radioactivity of the cells was determined using a gamma counter.

For an initial screen, each compound was added at a concentration of 800 micromolar, and given a timed uptake period of over 60 minutes. If less than 50% heme uptake inhibition was observed, or if any toxic effects were observed on the cell monolayer, no further evaluation of the specific porphyrin compound was undertaken. If greater than a 50% decrease in the uptake of iron was observed, then a titration of the inhibitor was undertaken, with an incubation time of 30 minutes. The concentration of inhibitor required to get a 50% decrease in heme uptake inhibition counts was then determined.

Figure 2:
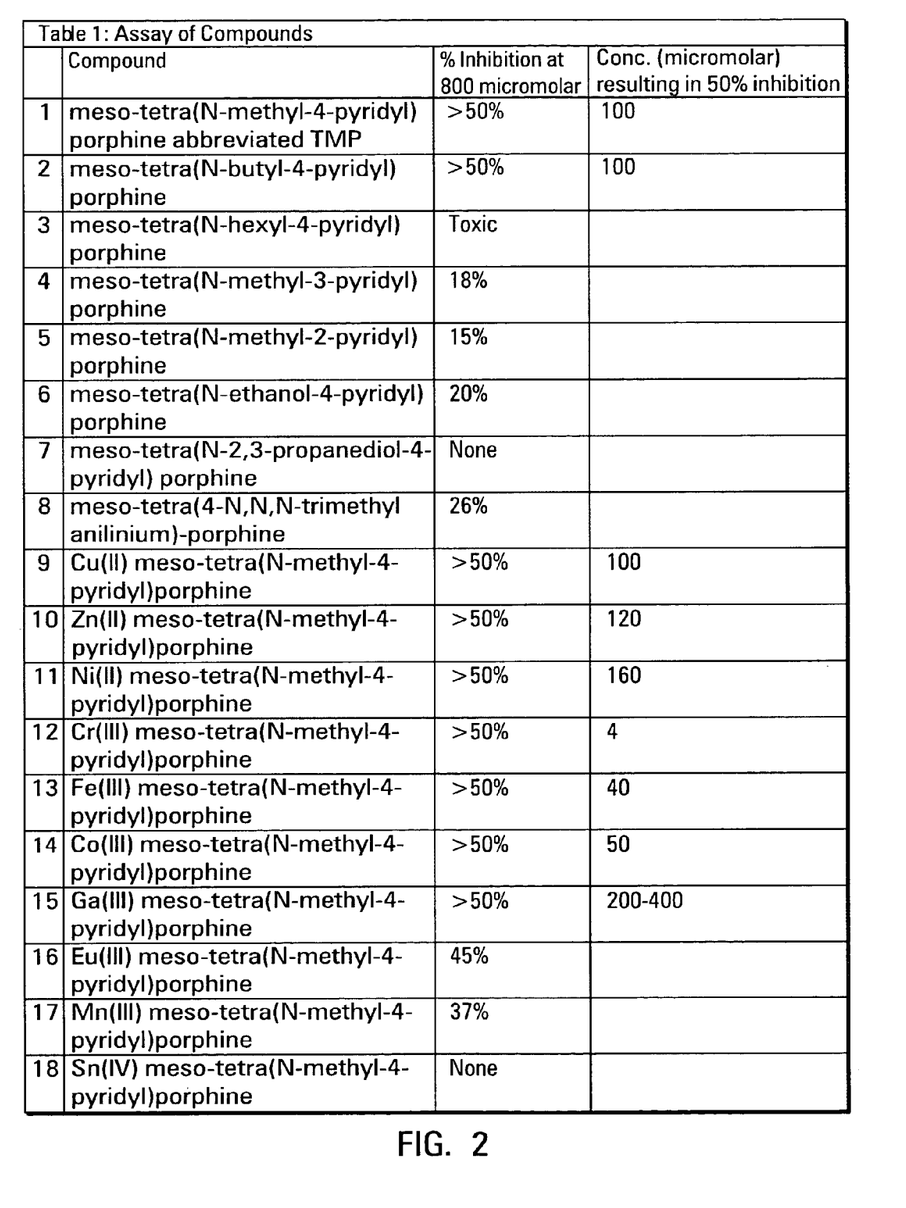
FIG. 2 contains Table 1, containing the results of an assay of various meso-tetra porphine agents and metalloporphyrins for ability to inhibit heme iron uptake in IEC-6 small intestinal derived cells incubated with radioactive iron-labeled heme solubilized in taurodeoxycholate micelles, listing the percent of inhibition of heme iron uptake when administered at 800 micromolar concentration and the results of a titration of agents providing greater than 50% inhibition to determine the concentration of the particular agent needed to provide 50% inhibition.
Figure 4:
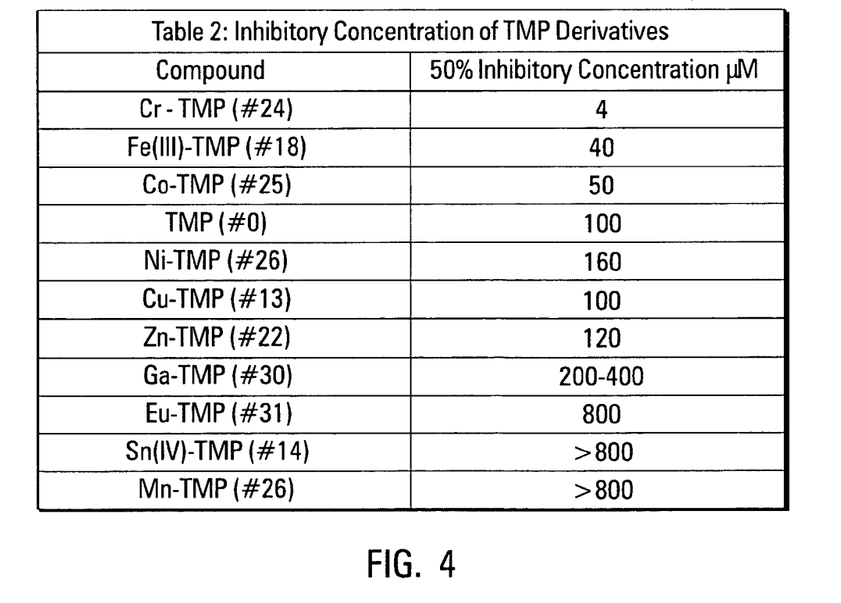
FIG. 4 contains Table 2, which presents the results of an assay for inhibition of heme iron uptake by various TMP-derivative agents, including various metalloporphyrins, showing the concentration of an agent necessary to provide 50% inhibition of heme iron uptake.

Tables 1 and 2 summarize the results from these studies. Table 1 is found in FIG. 2, and Table 2 is found in FIG. 4. As seen in FIGS. 2 and 4, meso-tetra(N-methyl-4-pyridyl) porphine inhibits heme uptake at a concentration of about 750 $\mu$M. Similarly, the analogous tetra-N-alkyl-4-pyridyl porphines and selected porphine metal complexes inhibit heme-iron uptake. As a result of this, these agents appear to constitute potential candidates for heme-iron uptake inhibition in humans.

Chelates of the free base porphyrin with Ga, Eu, Sn, or Mn show a decrease in the ability to inhibit the uptake of heme-iron. Chelates with Ni, Cu, and Zn, however, show inhibitory ability similar to that of the free base porphyrin, while chelates of Fe and Co show a two-fold increase in inhibitory activity when compared with that of the base. The Cr porphyrin chelate was effective to still another order of magnitude, and appeared to function as an efficient inhibitor that was active in the low micromolar range. Thus, in some embodiments of the invention, Cr (III) meso-tetra(N-methyl-4-pyridyl) porphine appears to be a promising candidate for use as a therapeutic agent. Other agents exhibiting heme uptake inhibitory activity at less than one millimolar concentration may also prove suitable for use in the molecules, compositions, and methods within the scope of the invention as a result of other physiologic effects yet to be discovered.

Figure 3:
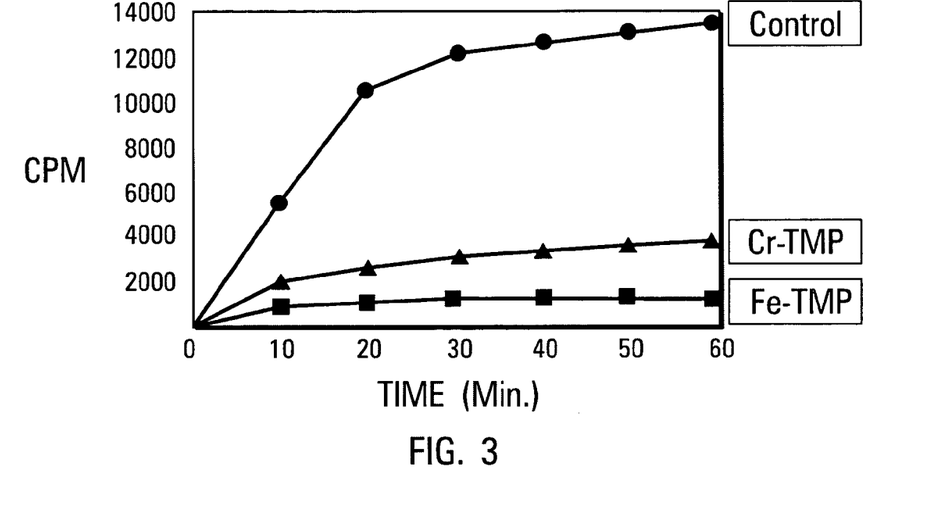
FIG. 3 is a chart illustrating the timed uptake of iron from heme by IEC-6 cells with a control and in the presence of a Cr-TMP inhibitor. The adsorption of iron from micellar heme was determined. 800 $\mu$M of Cr-TMP or Fe-TMP was added to parallel wells. The cells were incubated for the indicated time at 37 degrees, washed, and subsequently, the solubilized cells were counted in a gamma counter. Each point on the chart represents the average of duplicate data points.

The utility of the Cr-TMP metalloporphyrin was further studied to determine its usefulness in iron uptake inhibition. As shown in FIG. 3, the addition of 800 $\mu$M Cr-TMP with timed uptake shows inhibition to approximately background. In this experiment, 800 $\mu$M Cr-TMP (middle curve of FIG. 3) and Fe-TMP (lowest curve of FIG. 3) were added to parallel wells comprising IEC-6 cells. The cells were incubated for the time periods shown along the X-axis of the graph shown in FIG. 3. The inhibition exhibited by the agents of the invention was evident from the initial time points and persisted over the 60 minutes of the experiment. No toxicity to the cell monolayer was observed under the inverted microscope, and the metalloporphyrin only minimally stained the IEC-6 cell layer.

Figure 5:
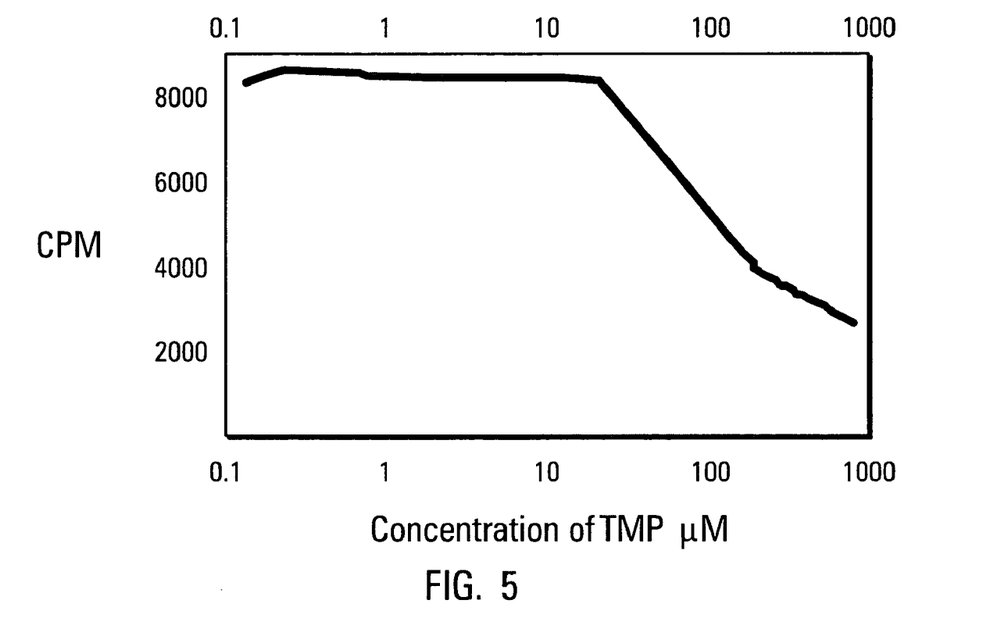
FIG. 5 is a chart illustrating the inhibition of heme iron uptake by TMP. IEC-6 cells were incubated with increasing amounts of TMP, and the uptake of iron was determined after 30 minutes using methods similar to those used in the assay documented in FIG. 2. Heme iron uptake is inhibited in IEC-6 cells by about 50% at a TMP concentration of about 100 $\mu$m.
Figure 6:
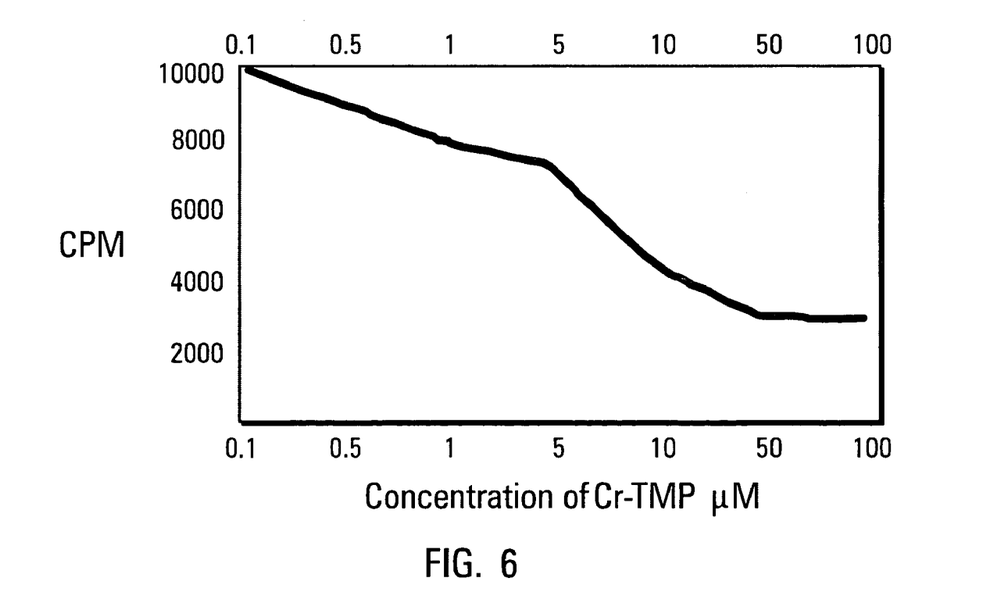
FIG. 6 is a chart illustrating the inhibition of heme iron uptake by Cr-TMP. In this assay, IEC-6 cells were incubated with increasing amounts of Cr-TMP and the uptake of iron was determined after 30 minutes using methods similar to those used in the assay documented in FIG. 2. Heme iron uptake is inhibited in IEC-6 cells by about 50% at a TMP concentration of about 4 $\mu$M.

Referring now to FIG. 5, titration of TMP (or free base porphyrin) showed 50% inhibition at a concentration of about 100 micromolar. This result was contrasted with the results observed in a similar experiment using Cr-TMP. The results of the Cr-TMP titration are shown in FIG. 6. As illustrated in the graph of FIG. 6, Cr-TMP inhibited uptake at a concentration of about 4 $\mu$M. In both of these experiments, IEC-6 cells were incubated with increasing amounts of either TMP or Cr-TMP. The uptake of iron was determined after 30 minutes.

Example 2

Inhibition of In Vivo Uptake of Radiolabeled Iron From Heme in the Rat Duodenal Model In this assay, Wistar rats were first anesthetized with pentobarbital. Wistar rats are from a strain originally developed at the Wistar Institute and commonly used all over the world for research. Following anesthesia, a midline incision was made in each of the rats. The duodenum of each animal was isolated between the pylorus and the ligament of Trietz by umbilical tape. The bile duct of each animal was then identified and ligated. Following this, a syringe was passed through the pylorus of each animal, and one ml of radiolabeled heme solution was introduced into the duodenum. The heme solutions used contained either only heme, or additionally included an appropriate concentration of an inhibitor to be evaluated.

Figure 7:
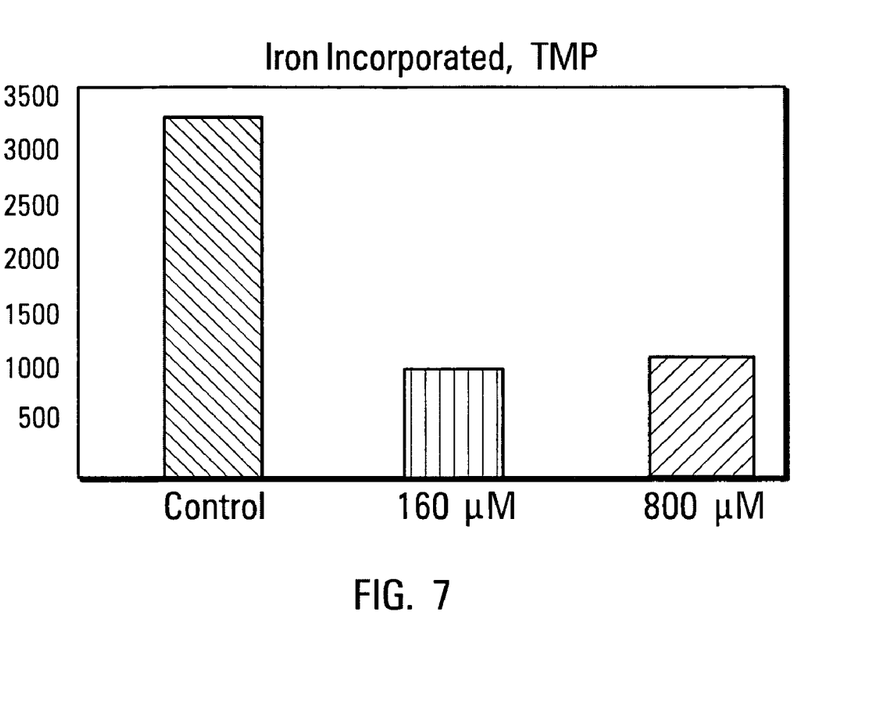
FIG. 7 includes a graph illustrating the inhibition of heme iron uptake in a rat duodenum induced by the presence of TMP. Isolated rat duodenum was incubated in vivo with radioactive solubilized heme and the several concentrations of TMP indicated in the graph. After 10 minutes, the duodenum was removed and the amount of iron absorbed was determined by measuring the amount of radioactivity present in the rat's body.
Figure 8:
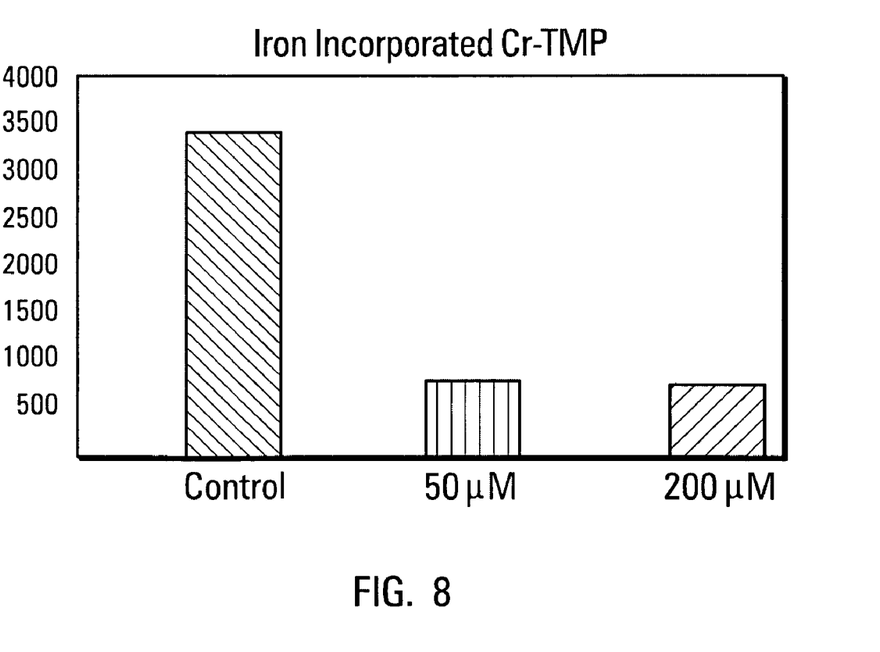
FIG. 8 includes a graph illustrating the inhibition of heme iron uptake in a rat duodenum induced by the presence of Cr-TMP. The experiment was performed as in the assay illustrated in FIG. 7, except that in these experiments, Cr-TMP was added with the solubilized heme in the concentrations indicated in the graph. After 10 minutes of incubation, the duodenum was removed and the amount of iron absorbed was determined by measuring the amount of radioactivity present in the rat's body.

Following introduction of the heme or heme/inhibitor solution, the duodenal loop of each animal was tied off. Heme absorption was allowed to continue for a period of 10 minutes. Following this absorption period, the duodenal loop of each rat was removed and the animal was killed. The rat carcass was counted in a whole body counter to determine the amount of radiolabeled heme isotope absorbed into the body from the duodenum. These methods were used to measure the efficacy of two potential heme iron uptake inhibitors: TMP (free base porphyrin), and Cr-TMP. The results of these two assays are seen in FIGS. 7 and 8, respectively.

TMP (free base porphyrin) was used at 160 and 800 $\mu$M concentrations in the taurodeoxycholate-solubilized heme solution. The results of this assay are shown in FIG. 7. As seen in the graph of FIG. 7, inhibition of iron uptake was observed on the incorporation of iron from heme into the body of the animal. At the higher concentration tested (800 $\mu$M), the TMP showed a slight precipitate, and there was considerable variation in inhibition noted in the group of animals tested.

Similar experiments were performed to test Cr-TMP for inhibitory ability. The Wistar rats were divided into three groups of 4 animals each. Group 1 was used as a control group. Group 2 was given Cr-TMP inhibitor at a concentration of about 50 $\mu$M along with the heme. Group 3 was given Cr-TMP inhibitor at a concentration of about 200 $\mu$M along with the heme. The results of this assay are shown in FIG. 8. The methods described with reference to the experiment documented in FIG. 7 were generally followed.

Following incubation of the heme/inhibitor solutions to the rats, the absorption of heme into the rats was measured. As illustrated in FIG. 8, it was found that the incorporation of radiolabeled heme into the animals showed almost complete inhibition at 50 and 200 $\mu$M concentrations. Without being limited to any one theory, it would appear that the lack of further decrease between 50 and 200 $\mu$M suggests that this is the background level.

Figure 9:
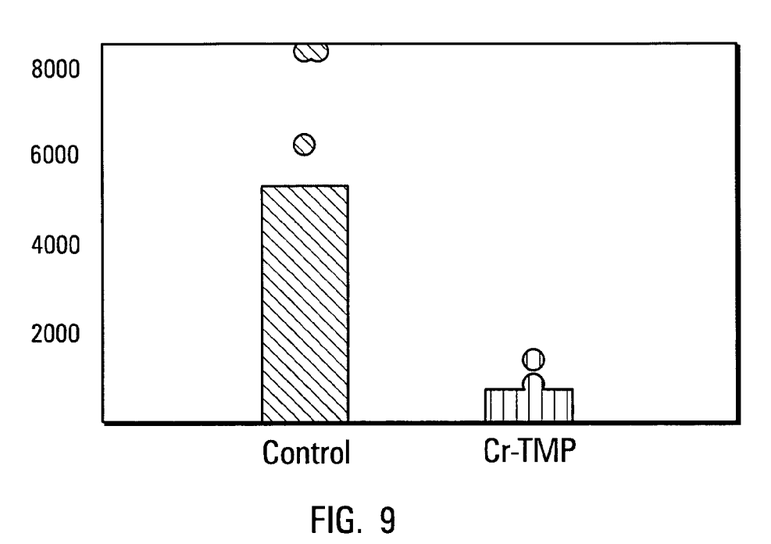
FIG. 9 includes a graph illustrating the inhibition of heme iron uptake in a rat duodenum induced by the presence of Cr-TMP. The experiment was performed as in FIGS. 7 and 8, with the exception that five rats were used in each group, and the incubation time was increased to 15 minutes. The points noted on the graph represent individual animals, while the bars represent the mean value. The p value between control and Cr-TMP was determined to be 0.018.

The results obtained in the experiment of FIG. 8 were confirmed in a second experiment, the results of which are shown in FIG. 9. In this experiment, 5 animals were utilized in each of the control and testing groups. The incubation time period was extended to be fifteen minutes. The inhibitor/heme solution had included Cr-TMP as the inhibitor at a concentration of about 50 $\mu$M. The points seen in FIG. 9 represent the measurements obtained individual rats, while the shaded bars represent the mean value for each group of animals. As would be understood to one of ordinary skill in the art, in vivo inhibition of heme iron uptake may potentially be obtained at even lower concentrations of Cr-TMP. The p value between control and Cr-TMP was determined to be 0.018. The results shown in FIG. 9 demonstrate that inhibition of heme-iron uptake by Cr-TMP is feasible in vivo, as shown in the Wistar rat duodenal model.

Example 3

Cell Toxicity

Figure 10:
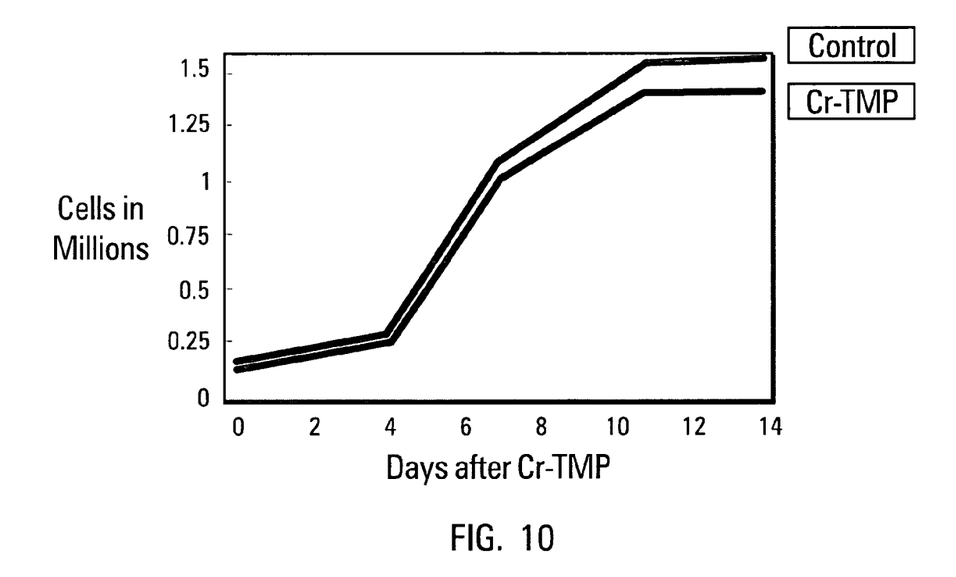
FIG. 10 is a chart showing the results of an experiment produced to test the toxicity of Cr-TMP to K562 cells. Cells were grown in the presence (lower line) or absence (upper line) of 50 $\mu$M Cr-TMP, and observed to reach a stationary phase of growth at about day 10.

In a next set of experiments, K562 cells were used to test toxicity of the porphyrins of the invention. The results of this test are shown in FIG. 10. K562 cells are erythroleukemia cells from a cell line derived from a chronic myeloid leukemia patient in blast crisis. K562 cells were selected for this testing based on their ability to grow in suspension. This characteristic renders cell counting more reliable. Referring to FIG. 10, samples of the cells were grown in the presence (lower curve) or absence (upper curve) of Cr-TMP at a concentration of 50 $\mu$M. The cells were incubated, and were observed to have reached stationary phase at about day 10.

It was observed that the growth rate of the cells was not decreased even in growth media containing 50 micromolar Cr-TMP (FIG. 10). Some inhibition of cell growth was seen at concentrations above this, but even then growth was merely slowed, while the cells remained viable. No toxicity was seen even after two weeks of exposure, at which point the cells entered stationary phase.

Figure 11:
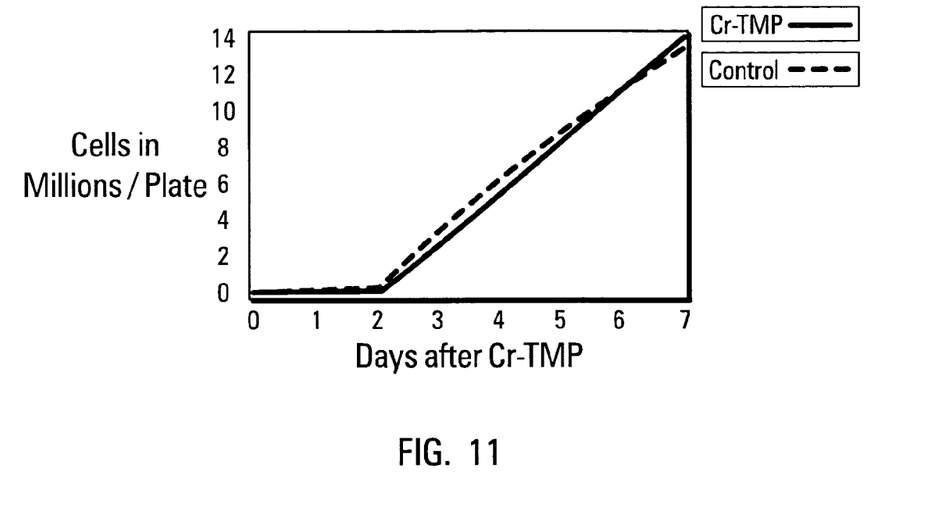
FIG. 11 is a chart showing the results of an experiment produced to test the toxicity of Cr-TMP to IEC-6 cells. Cells were grown in the presence (right) or absence (left) of 50 $\mu$M Cr-TMP.

IEC-6 (small intestinal cells) grown in monolayers were also tested for Cr-TMP toxicity. The results of this testing are shown in FIG. 11. Cells were plated overnight, and the Cr-TMP was added to the media at a concentration of 100 $\mu$M. Observations could only be made for a period of 7 days' exposure to the inhibitory porphyrin agents of the invention due to the instability of the monolayers, which became hyper-confluent in both the treated and control cultures.

Figure 12:
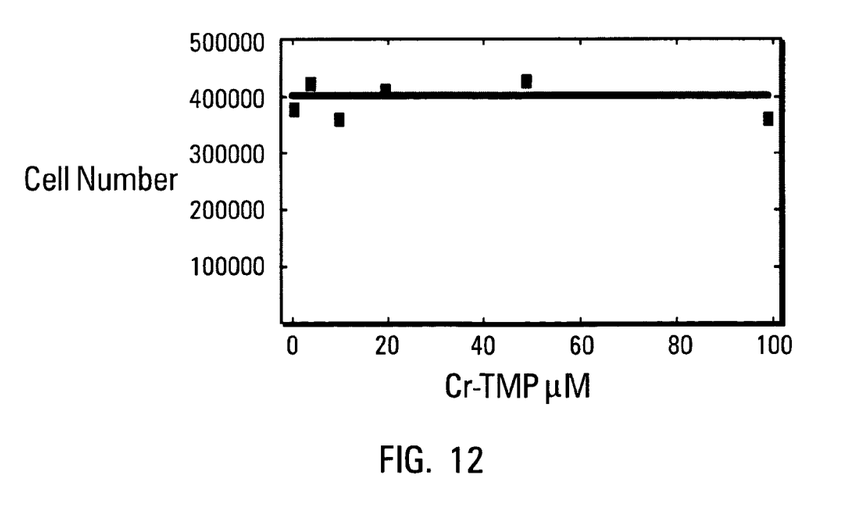
FIG. 12 is a chart showing the results of an experiment produced to test the toxicity of Cr-TMP to IEC-6 cells at day 4. This figure shows that no toxicity is observed in concentrations of up to about 100 $\mu$M.

As is observed in FIG. 11, during this period of time, no decrease in growth rate or extent was observed in cells with Cr-TMP exposure at a concentration of 50 $\mu$M. Similarly, as shown in FIG. 12, no toxicity was observed in cells exposed to concentrations of up to about 100 $\mu$M.

Example 4

Uptake of the Inhibitor

To minimize possible side effects of heme uptake inhibition drugs, it would be advantageous if the drugs were minimally absorbed by the body, while still remaining able to perform their designated function. In order to determine the amount of Cr-TMP absorbed in vivo across the intestinal wall, duodenal loops in six rats in each of two groups were incubated for 15 minutes with either 6.5 millimolar taurodeoxycholate or 6.5 millimolar taurodeoxycholate plus 50 micromolar Cr-TMP.

Subsequently, cardiac punctures were performed on the rats, and between 0.45 and 1.3 ml of blood were collected from each. The plasma of the blood samples was separated and precipitated overnight with 10% trichloroacetic acid. After centrifugation, the optical absorbance at 447 nm and the peak absorbance of the very strong soret peak of Cr-TMP were determined. There was no difference observed between the control and treated groups. The measurements had a limit of sensitivity of $4\times10^{-8}$ molar. This result indicates that essentially no absorption of the Cr-TMP took place.

Example 5

Synthesis of Inhibitors

The tetra-positively charged porphyrins of the invention are based upon the commercially available porphyrin 5,10,15,20-tetra(4-pyridyl)-21H, 23H-porphine and were N-alkylated using standard techniques. Some such techniques are taught in Pasternack, R. F., P. R. Huber, P. Boyd, G. Engasser, L. Francesconi, E. Gibbs, P. Fasella, G. Cerio Venturo, and L. deC. Hinds, *J. Am. Chem. Soc.*, 94:4511–4517 (1972); and Meng, G. G., B. R. James, K. A. Shov, and M. Korbelik, *Can. J. Chem.*, 72:2447–2457 (1994), each of which is incorporated herein in its entirety by this reference.

Metallations of the porphyrins were performed using standard porphyrin metal incorporation procedures, such as those outlined in *"Porphyrins and Metalloporphyrins"* Ed. Kevin M. Smith 1975, Elsevier Scientific Publishing ISBN 0-444-41375-8, pages 157–231, which is incorporated herein in its entirety by this reference.

The present invention may be embodied in other specific forms without departing from its structures, methods, or other essential characteristics as broadly described herein. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope. All publications, patents and patent applications cited herein, whether supra or infra, are hereby incorporated by reference in their entirety. As used in this specification and the appended claims, the singular forms "a," "an," and "the" include plural references unless the content clearly dictates otherwise.

What is claimed is:

1. A method for inhibiting the cellular uptake of iron in a human or a non-human mammal, comprising the step of administering a tetra-positively charged porphyrin having the formula 5,10,15,20-tetrakis(1-alkyl-4-pyridyl)-21H, 23H-porphine, wherein the alkyl is selected from the group consisting of methyl, ethyl, propyl, and butyl; to a mammal in need of such treatment.

2. The method of claim 1, wherein propyl is n-propyl or isopropyl.

3. The method of claim 1, wherein butyl is n-butyl, isobutyl, or t-butyl.

4. The method of claim 1, wherein the porphyrin is a metal chelated porphyrin.

5. The method of claim 1, wherein the metal chelated porphyrin is a metal chelate of a metal selected from the group consisting of Cu(II), Zn(II), Ni(II), Cr(III), Fe(III), Co(III), Ga(III), Eu(III), Mn(III), and Sn(IV).

6. The method of claim 5, wherein propyl is n-propyl or isopropyl.

7. The method of claim 5, wherein butyl is n-butyl, isobutyl, or t-butyl.

8. A method of treating an iron-overload disease in a human or a non-human mammal by administering a compound that inhibits cellular uptake of heme-iron, comprising the steps of administering a primary de-ironing treatment and administering a tetra-positively charged porphyrin having the formula 5,10,15,20-tetrakis(1-alkyl-4-pyridyl)-21H,23H-porphine, wherein the alkyl is selected from the group consisting of methyl, ethyl, propyl, and butyl; to the human or non-human mammal in need of such treatment.

9. The method of claim 8, wherein the primary de-ironing treatment is serial phlebotomy.

10. The method of claim 8, wherein the primary de-ironing treatment is chelation therapy conducted using a chelating agent.

11. The method of claim 10, wherein the chelating agent is deferoxamme.

12. The method of claim 8, wherein propyl is n-propyl or isopropyl.

13. The method of claim 8, wherein butyl is n-butyl, isobutyl, or t-butyl.

14. The method of claim 8, wherein the porphyrin is a metal chelated porphyrin.

15. The method of claim 14, wherein the metal chelated porphyrin is a metal chelate of a metal selected from the group consisting of Cu(II), Zn(II), Ni(II), Cr(III), Fe(III), Co(III), Ga(III), Eu(III), Mn(III), and Sn(IV).

16. The method of claim 15, wherein propyl is n-propyl or isopropyl.

17. The method of claim 15, wherein butyl is n-butyl, isobutyl, or t-butyl.

18. The method of claim 15, wherein the porphyrin is a metal chelated porphyrin.

* * * * *

UNITED STATES PATENT AND TRADEMARK OFFICE
CERTIFICATE OF CORRECTION

| | | |
|---|---|---|
| PATENT NO. | : 7,008,937 B2 | Page 1 of 1 |
| APPLICATION NO. | : 10/859810 | |
| DATED | : March 7, 2006 | |
| INVENTOR(S) | : Jerry C. Bommer | |

It is certified that error appears in the above-identified patent and that said Letters Patent is hereby corrected as shown below:

In column 1, line 17, please replace "fights" with --rights--

In column 14, line 62, please replace "claim 1" with --claim 4--

Signed and Sealed this

Seventeenth Day of October, 2006

JON W. DUDAS
*Director of the United States Patent and Trademark Office*